(12) United States Patent
Das

(10) Patent No.: US 7,666,910 B2
(45) Date of Patent: *Feb. 23, 2010

(54) METHOD OF STABILIZING AND POTENTIATING THE ACTION OF ANTI-ANGIOGENIC SUBSTANCES

(76) Inventor: Undurti Narasimha Das, c/o EFA Sciences LLC, 1420 Providence Hwy., Suite #266, Norwood, MA (US) 02062

( * ) Notice: Subject to any disclaimer, the term of this patent is extended or adjusted under 35 U.S.C. 154(b) by 1634 days.

This patent is subject to a terminal disclaimer.

(21) Appl. No.: 10/083,529

(22) Filed: Feb. 27, 2002

(65) Prior Publication Data

US 2003/0096869 A1 May 22, 2003

Related U.S. Application Data

(62) Division of application No. 09/478,291, filed on Jan. 5, 2000, now Pat. No. 6,380,253.

(51) Int. Cl.
*A61K 31/20* (2006.01)
*A61K 31/225* (2006.01)
*A61K 9/70* (2006.01)

(52) U.S. Cl. .................. 514/560; 424/422; 424/445; 424/449; 514/547

(58) Field of Classification Search .............. 514/560, 514/547; 424/422, 445, 119
See application file for complete search history.

(56) References Cited

U.S. PATENT DOCUMENTS 6,380,253 B1 * 4/2002 Das .................. 514/560
6,426,367 B1 * 7/2002 Das .................. 514/560
6,617,354 B1 * 9/2003 Das .................. 514/560

FOREIGN PATENT DOCUMENTS

JP 63303925 * 12/1988

OTHER PUBLICATIONS

Yanai et al, Anti-tumor effect of arterial administration of a medium-chain triglyceride solutionof an angiogenesis inhibitor, Pharmaceutical Research, 1995, 12 No. 5, 653-7. (abs).*
Kokura et al, Efficacy of hyperthermia and polyunsaturated fatty acids on experimental carcinoma, Cancer Research, 1997, 57 No. 11, 2200-2. (abs).*

* cited by examiner

*Primary Examiner*—Alton N Pryor

(57) ABSTRACT

A method of stabilizing and potentiating action of molecules of known anti-angiogenic substances such as ANGIOSTATIN® or ENDOSTATIN® by using in coupling conjugation with cis-unsaturated fatty acids (c-UFAs) in the treatment of cell proliferative disorders uses c-UFAs chosen from linoleic acid, gamma-linolenic acid, dihomo-gamma-linolenic acid, arachidonic acid, alpha-linolenic acid, eicosapentaenoic acid, docosahexaenoic acid and cis-parinaric acid in predetermined quantities. Preferably, the c-UFAs are in the form of polyunsaturated fatty acids (PUFAs). Uncontrolled or undesirable angiogenic activity promotes cell proliferative disorders and tumor growth, which can be inhibited by the selective use of PUFAs with anti-angiogenic substances used selectively in conjunction with predetermined anti-cancer drugs. For a non-glioma type of cell proliferation disorder, a sodium, potassium or lithium salt of a PUFA is preferred to form an admixture with an anti-angiogenic substance. Anti-angiogenic substances envisaged in this invention include ANGIOSTATIN, ENDOSTATIN, platelet factor-4, TNP-470, thalidomide, interleukin-12 and metalloproteinase inhibitors (MMP). A preferred method of administration of the mixture to treat a tumor is intra-arterial administration into an artery which provides the main blood supply for the tumor.

7 Claims, No Drawings

METHOD OF STABILIZING AND POTENTIATING THE ACTION OF ANTI-ANGIOGENIC SUBSTANCES

This application is a divisional of U.S. application Ser. No. 09/478,291 filed on 5 Jan. 2000 now U.S. Pat. No. 6,380,253.

FIELD OF THE INVENTION

The present invention generally relates to the use of anti-angiogenic agents in the cure of cell proliferative disorders including cancer and other disorders caused by uncontrolled angiogenic activity in the body. More particularly, the invention is directed to the efficacious use of anti-angiogenic agents.

RELATED APPLICATIONS

This invention relates to co-pending U.S. application Ser. No. 09/392,953 filed on Sep. 9, 1999 and entitled "Method of Treatment for Cell proliferative Disorders including Cancer", which is incorporated herein by reference.

BACKGROUND OF THE INVENTION

The term angiogenesis refers to the generation or formation of new blood vessels into a tissue or organ. Angiogenesis can occur both during some physiological processes and/or in some pathological conditions. For example, angiogenesis can be seen to occur during wound healing, fetal growth, corpus luteum, and endometrium, etc., (1). Endothelial cells, which cause to form the inner lining of the blood vessels, are constituted by a thin layer of epithelial cells and these cells are necessary for the process of angiogenesis. During the process of angiogenesis, irrespective of whether it is physiological or pathological, the endothelial cells release enzymes which can produce erosions of the basement membrane through which the endothelial cells cause protrusions. In response to the stimuli given by various agents, endothelial cells proliferate and migrate through the protrusions and form a sprout of the parent blood vessel. These endothelial cell sprouts can merge to form capillary loops leading to the formation of new blood vessel(s). If the blood vessels are in a tumor area, these new blood vessels in turn will provide enough nutrients and energy sources so that tumor cells can divide, proliferate and grow both in number and size.

Thus, the process of angiogenesis is both essential and critical to the growth of cancer. The other pathological states in which angiogenesis plays a critical role include: rheumatoid arthritis, psoriasis, scleroderma, myocardial angiogenesis, corneal diseases, diabetic retinopathy associated with neovascularization, macular degeneration, ovulation, menstruation etc. The process of angiogenesis also appears to be critical for tumor metastasis.

Since angiogenesis is such a critical process in the promotion of cancer and tumor metastasis, several researches have been trying to devise methods or develop drugs which can selectively suppress angiogenesis with the hope that this would eventually lead to the inhibition of tumor growth. There are other situations where uncontrolled angiogenesis is undesirable. For instance, formation of new blood vessels in an area like cornea during the process of healing of the corneal ulcer, if it is in excess, can lead to corneal scar formation.

In the case of rheumatoid arthritis, angiogenesis can lead to continued inflammation in the joints and also to osteoporosis. In such an instance, prevention of formation of new blood vessels will lead to reduction in inflammation and also prevention of fibrous ankylosis and bony ankylosis. Thus, selective prevention and control of angiogenesis may be of benefit in the aforementioned conditions, as well as in several other conditions such as: uterine fibroids, psoriasis, scleroderma, diabetic retinopathy, keloids, ovulation etc. Another area where prevention of angiogenesis will be of benefit is in the inhibition of ovulation and menstruation and growth of placenta and this will lead to prevention of fertilization and growth of the fetal tissue. This may, thus, form a new approach in the development of fertility control measures.

Two naturally occurring molecules which have been identified to adversely influence or inhibit angiogenesis are ANGIOSTATIN® and ENDOSTATIN® (2). Both these molecules are proteins. ANGIOSTATIN is a protein of molecular weight approximately 38 kD and has an amino acid sequence substantially similar to that of a fragment of murine plasminogen beginning at amino acid number 98 of an intact murine plasminogen molecule. The amino acid sequence of ANGIOSTATIN varies only slightly between species. The amino acid sequence of the human ANGIOSTATIN is substantially similar to the murine plasminogen fragment. But, it may be mentioned here that the active human ANGIOSTATIN sequence starts either at the amino acid number 97 or 99 of an intact human plasminogen amino acid sequence. In addition, human plasminogen has potent anti-angiogenic activity even in a mouse tumor model. This explains why both murine and human plasminogens and ANGIOSTATIN/ENDOSTATIN molecules show fairly similar anti-angiogenic activities in a variety of animal tumor models (3).

U.S. Pat. No. 5,792,845 issued on Aug. 11, 1998 to O'Reilly et al, teaches that therapies directed at control of the angiogenic process could lead to the abrogation or mitigation of certain diseases. O'Reilly et al suggests that modulation of the formation of capillaries in angiogenic processes (such as wound healing and reproduction) is useful since undesired and uncontrolled angiogenesis can cause certain diseases to progress. O'Reilly et al teaches that ANGIOSTATIN protein has the capability of inhibiting angiogenesis, eg., to inhibit the growth of bovine capillary endothelial cells in culture in the presence of fibroblast growth factor.

U.S. Pat. No. 5,792,845 issued on Aug. 11, 1998 to O'Reilly et al, teaches that therapies directed at control of the angiogenic process could lead to the abrogation or mitigation of certain diseases. O'Reilly et al suggests that modulation of the formation of capillaries in angiogenic processes (such as wound healing and reproduction) is useful since undesired and uncontrolled angiogenesis can cause certain diseases to progress. O'Reilly et al teaches that ANGIOSTATIN protein has the capability of inhibiting angiogenesis, e.g., to inhibit the growth of bovine capillary endothelial cells in culture in the presence of fibroblast growth factor.

U.S. Pat. No. 5,932,545 issued on Aug. 3, 1999 to Henkin et al teaches an anti-angiogenic drug in the form of a peptide or a salt thereof, to treat cancer, arthritis and retinopathy. The Henkin et al patent states however that angiogenesis inhibitors could cause systemic toxicity in humans. ANGIOSTATIN in the O'Reilly patent '845 is described and claimed as an Isolated nucleotide molecule with a specific sequence. It has been stated however that the ANGIOSTATIN molecule as known at present is not suitable for clinical trials.

ENDOSTATIN, which is also similar to ANGIOSTATIN, has been shown to cause a dramatic reduction of primary and metastatic tumors in experimental animals. ENDOSTATIN is a 20 kDa C-terminal fragment of collagen XVIII. ENDOSTATIN could specifically inhibit endothelial cell proliferation and angio-genesis and thus, block tumor growth (2, 4).

It is important to note that ANGIOSTATIN is derived from plasminogen or plasmin. It has been shown that human prostate carcinoma cell lines express enzymatic activity that can generate bioactive ANGIOSTATIN from purified human plasminogen or plasmin. This bioactive ANGIOSTATIN has been shown to inhibit human endothelial cell proliferation, basic fibroblast growth factor-induced migration, endothelial cell tube formation, and basic fibroblast growth factor-induced corneal angiogenesis. In an extension of this study, it was noted that a serine proteinase is necessary for ANGIOSTATIN generation (5).

ANGIOSTATIN, derived from plasminogen, selectively inhibits endothelial cell proliferation. When ANGIOSTATIN is given systemically it shows potent inhibitory action on the growth of tumor and renders metastatic and primary tumors to go into a dormant state by striking a balance between the rate of proliferation and apoptosis of the tumor cells (6). The very identification of ANGIOSTATIN has come from the observation that when a primary tumor is present, the growth of metastases is suppressed. On the other hand, after tumor removal, the previously dormant metastases develop new blood vessels (neovascularization) and grow. Both serum and urine from the tumor-bearing animals, but not from controls, showed very specific inhibitory action on the growth of endothelial cells. Subsequent studies led to the purification of this inhibitor of endothelial cells which was later identified as a 38 kD plasminogen fragment namely ANGIOSTATIN. It is now known that ANGIOSTATIN, which can also be obtained by a limited proteolytic digestion of human plasminogen, but not intact plasminogen can be administered systemically to block neovascularization and growth of metastases and primary tumors. A recombinant human ANGIOSTATIN which comprises of kringles 1-4 of human plasminogen (amino acids 93-470) expressed in *Pichia pastoris* has been prepared and is now available for use. This recombinant ANGIOSTATIN showed the same physical properties as that of the natural ANGIOSTATIN in terms of molecular size, binding to lysine, reactivity with antibody to kringles 1-3 (3, 7). This recombinant ANGIOSTATIN when given to experimental animals, showed anti-angiogenic and anti-tumor activity (3). In addition, recombinant mouse ANGIOSTATIN was produced using the baculo-virus infected insect cells (8), which also (the secreted protein) showed potent inhibitory action on the proliferation of bovine capillary endothelial cells in vitro. The conversion of plasminogen to ANGIOSTATIN by PC-3 cells is now identified to be due to two components released, urokinase (uPA) and free sulfhydryl donors (FSDs). This is supported by the fact that even in a cell-free system, ANGIOSTATIN can be generated from plasminogen by plasminogen activators (u-PA, tissue-type plasminogen activator, tPA or streptokinase) in combination with any one of free sulfhydryl donors such as N-acetyl-L-cysteine, D-penicillamine, captopril, L-cysteine, or reduced glutathione. This cell-free derived ANGIOSTATIN also showed anti-angiogen activity both in vitro and in vivo and suppressed the growth of Lewis lung carcinoma metastases (9).

ANGIOSTATIN administration to mice with subcutaneous hemangioendothelioma and associated disseminated intravascular coagulopathy revealed that in addition to a significant reduction in the size of the tumor, increased survival, decrease in thrombocytopenia and anemia was noted (10). This indicates that ANGIOSTATIN may also be useful to treat disseminated intravascular coagulopathy.

One of the mechanisms by which ANGIOSTATIN inhibits endothelial cell proliferation includes its ability to affect by 4 to 5 fold the expression of E-selectin in proliferating endothelial cells (11). On the other hand, ANGIOSTATIN did not alter cell cycle progression significantly. Further, ANGIOSTATIN also enhanced the adhesion activity in proliferating endothelial cells.

Rivas et al (12) studied the possible relationship between human macropahge metalloelastase (HME) expression, a member of the human matrix metalloproteinase family, which is believed to play an important role in ANGIOSTATIN generation, and ANGIOSTATIN production. Their study showed that patients whose tumors did not express HME mRNA and so did not produce ANGIOSTATIN, had poorer survival than those whose tumors showed high expression of HME mRNA and ANGIOSTATIN generation. This study suggests that HME gene expression is closely associated with ANGIOSTATIN generation and prognosis in patients with hepatocellular carcinoma (HCC). This relationship between HME and ANGIOSTATIN is understandable since, metalloproteinase(s) can block angiogenesis by converting plasminogen to ANGIOSTATIN (12,13,14).

Another mechanism by which recombinant human and murine ANGIOSTATINs can block angiogenesis is by inducing apoptosis (programmed cell death) of endothelial cells (15), similar to that seen with tumor necrosis factor (TNF) and transforming factor-beta 1 (TGF-beta1), which are also known to induce apoptosis in endothelial cells.

Yet another mechanism by which ANGIOSTATIN can produce apoptosis and inhibit angiogenesis is probably by binding to ATP synthase. Using human umbilical endothelial vein endothelial cells, Moser et al (16) observed that ANGIOSTATIN bound in a concentration-dependent, saturable manner to the alpha/beta sub-units of ATP synthase. This binding of ANGIOSTATIN to the alpha/beta sub-unit of ATP synthase was inhibited by as much as 90% in the presence of anti-alpha-sub-unit ATP synthase antibody. This indicates that ANGIOSTATIN by binding to ATP synthase may actually shut-off ATP synthesis in the endothelial cells and this would eventually lead to death of the cells due to the non-availability of ATP, the main energy source for the survival of the cells. In addition, it was also reported that ANGIOSTATIN can inhibit extra-cellular-matrix-enhanced, t-PA catalysed plasminogen activation. This results in reduced invasive activity of endothelial cells (17). All these results indicate that ANGIOSTATIN has multiple actions by which it is able to block endothelial cell proliferation and angiogenesis.

Some of the factors which are known to inhibit the generation of ANGIOSTATIN include TGF-beta1 and plasminogen activator inhibitor type-1 (PAI-1), at least, by human pancreatic cancer cells in vitro (18).

Twining et al (19) showed that plasmin, the active form of plasminogen, is necessary for the maintenance of normal cornea and for corneal wound healing. It was also noted that plasmin is a major serine proteinase in the human cornea and that cornea can synthesize plasminogen. Both interleukin-1alpha and 1 beta stimulated corneal plasminogen synthesis by almost 2 to 3fold where as interleukin-6 decreased corneal plasminogen synthesis by 40%. Thus, cornea seems to have the ability to synthesize plasminogen, the precursor of plasmin and ANGIOSTATIN, and also regulate its synthesis in response to injury and inflammation and IL-1 and IL-6 (19).

Though both ANGIOSTATIN and ENDOSTATIN and other similar anti-angiogenic molecules provided an important therapeutic advance for cancer treatment, it should be emphasized here that the needed dosages of these proteins, especially ANGIOSTATIN used in the animal studies seem to be too high for clinical trials (20). Further, repeated injections and long-term treatment with ANGIOSTATIN are required to obtain its maximal anti-tumor effect. In view of this, methods to supplement the anti-angiogenic action of ANGIOSTATIN and ENDOSTATIN and other similar compounds are considered desirable. These methods include: use of ANGIOSTATIN along with other conventional anti-cancer drugs including radiation and novel methods of delivery of ANGIOSTATIN to tumor cells (21). Mauceri et al (22) studied the combined effect of radiation with ANGIOSTATIN and showed that this combination produced no increase in toxicity towards normal tissue. Both in vitro and in vivo studies showed that these agents (radiation and ANGIOSTATIN) in combination target the tumor vasculature. In an extension of this study, Gorski et al (23) demonstrated that the efficacy of experimental radiation therapy is potentiated by brief concomitant exposure of the tumor vasculature to ANGIOSTATIN.

Two novel methods of delivery of ANGIOSTATIN and similar compounds to the tumor cells that have been tried include:

(a) Nguyen et al (24) generated recombinant adeno-associated virus (rAAV) vectors that carry genes encoding for ANGIOSTATIN, ENDOSTATIN, and an antisense mRNA species against vascular endothelial growth factor (VEGF). These rAAVs efficiently transduced three human tumor cell lines that have been tested. Further, testing of the conditioned media from cells transduced with this rAAV or with rAAV-expressing ENDOSTATIN or ANGIOSTATIN inhibited effectively endothelial cell proliferation in vitro. These results indicate that rAAVs can be used to block angiogenesis and cancer growth.

(b) In a different approach, Chen et al (25) examined whether liposomes complexed to plasmids encoding ANGIOSTATIN or ENDOSTATIN can inhibit angiogenesis and growth of tumors. These studies revealed that plasmids expressing ANGIOSTATIN (PCI-angio) or ENDOSTATIN (PCI-endo) can effectively reduce angiogenesis and the size of the tumors implanted in the mammary fat pad of male mice to a significant degree. In addition, liposomes complexed to PCI-endo when given intravenously reduced tumor growth in nude mice by nearly 40% when compared to controls (25).

SUMMARY OF THE INVENTION

All the above factors and observations attest to the fact that malignant tumors are angiogenesis-dependent diseases. But, it should be mentioned here that tumor-associated angiogenesis is a complex, multi-step process which can be controlled by both positive and negative factors. It appears, as though, angiogenesis is necessary, but not sufficient, as the single event for tumor growth (26). But, it is evident from several experimental results that angiogenesis may be a common pathway for tumor growth and progression. Though several anti-angiogenic agents are being tried to arrest tumor growth, these are not without problems. Since the majority of these agents are proteins/peptides, their long-term use may lead to the development of antibodies which can neutralize their action. These anti-angiogenic substances need to be given repeatedly and some of them are unstable and are difficult to produce in large amounts.

In view of this, it is desirable and necessary to make efforts to stabilize and potentiate the actions of known anti-angiogenic molecules.

The present invention teaches the efficacious use of anti-angiogenic substances, which can inhibit endothelial cell proliferation and coupling them to cis-unsaturated fatty acids, which also have anti-angiogenic and cytotoxic actions on tumor cells, such that the actions of these substances are potentiated by each other. Further, as angiogenesis is involved in other disease processes such as inflammation, tumor metastasis, etc., it is envisaged that the conjugate(s) of anti-angiogenic substances and c-UFAs will be useful in these diseases also.

In this context, it is important to note that the inventor has found that polyunsaturated fatty acids (PUFAs) such as gamma-linolenic acid (GLA), dihomo-GLA (DGLA), arachidonic acid (AA), eicosapentaenoic acid (EPA) and docosahexaenoic acid (DHA) can selectively kill the tumor cells ((27-32) and under specific conditions and in conjugation with salts such as lithium and a lymphographic agent these fatty acids can actually behave as anti-angiogenic substances, i.e. they block all the blood supply to the tumor and also prevent generation of new blood vessels. Using these fatty acids in this particular combination, the inventor has successfully treated human hepatocellular carcinoma and giant cell tumor of bone with few or no side-effects.

Described hereinafter is a novel combination of a protein and a lipid and method(s) for its use. The protein referred to herein is a potent and specific inhibitor of endothelial proliferation and angiogenesis. The lipid may be one or more of the polyunsaturated fatty acids: LA (linoleic acid), GLA, DGLA, AA, ALA (alpha-linolenic acid), EPA, DHA and cis-parinaric acid. In this instance or method the polyunsaturated fatty acid needs to be given only once or at the most twice within a period of 1 to 2 months. This invention teaches that unlike ANGIOSTATIN/ENDOSTATIN, these fatty acids are not only cytotoxic to the tumor cells but are also able to function as anti-angiogenic agents (33-35). Further, polyunsaturated fatty acids when given in the formulated form, are more potent than ANGIOSTATIN/ENDOSTATIN in their anti-angiogenic and anti-cancer actions.

The invention in one aspect teaches a method of interrupting blood supply to a tumor region causing necrosis or apoptosis. The invention also provides a method of causing anti-angiogenic action in the tumor region with the result that new blood vessels and collaterals are not formed to sustain the tumor. The present invention in another aspect tackles the issue of drug delivery to the target tissue and provides the most efficacious method of administering an admixture of selected PUFAs with other elements such as anti-angiogenic substances as will be described hereinafter.

The invention in yet another aspect teaches a method of interrupting blood using a pre-determined admixture of at least a PUFA and an anti-angiogenic agent causing necrosis with very desirable results. Both the PUFAs and anti-angiogenic compounds being similar in function, the invention also provides a method of causing anti-angiogenic action in the tumor region with the result that new blood vessels and collaterals are not formed to sustain the tumor in the tumor region treated according to the invention. The present invention in another aspect tackles the issue of drug delivery to the target tissue and provides the most efficacious method of administering an admixture of selected PUFAs along with an anti-angiogenic substance and other elements as will be described hereinafter.

Tumor cells are deficient in phospholipase A2, an enzyme necessary for the release of various PUFAs from the cell membrane lipids as a result of which the production of anti-neoplastic PGs such as PGD2 are not elaborated. In addition, tumor cells secrete an excess of PGE2, an immunosuppressive and mutagenic substance. Further, tumor cells are deficient in PUFAs such as GLA, AA, EPA and DHA due to the low activity of delta-6-desaturase. As a result of these metabolic changes, tumor cells are able to effectively circumvent body's defense and survive. The present invention provides a method of causing necrosis of tumor cells despite their known survival pattern.

Anti-Cancer Actions of PUFAs

Tumor cells are not only deficient in PUFAs but also have low rate(s) of lipid peroxidation, contain relatively large amounts of antioxidants such as vitamin E and superoxide dismutase (SOD). It is also believed that low rates of lipid peroxidation and consequent low amounts of lipid peroxides in the cells can contribute to an increase in the mitotic process which ultimately leads to an increase in cell proliferation. Thus, a deficiency of PUFAs, high amounts of antioxidants and the presence of low amounts of lipid peroxides in the tumor cells can contribute to the growth of tumor cells. This is supported by studies by the inventor wherein it was noted that PUFAs such as GLA, DGLA, AA, EPA and DHA can decrease tumor cell proliferation. In addition, it was also observed that when appropriate amounts of GLA, DGLA, AA, EPA and DHA were administered to tumor cells and normal cells, obtained from American Type Culture Collection, only tumor cells were killed without having any significant action on the survival of normal cells in vitro. In mixed culture experiments, in which both normal and tumor cells were grown together, GLA showed more selective tumoricidal action compared to AA, EPA and DHA though, these latter fatty acids were also effective to some extent. This indicated that selective delivery of GLA, DGLA, AA, EPA and DHA to tumor cells may offer a new therapeutic approach in the treatment of cancer.

These in vitro results are supported by in vivo studies performed in animal tumor models. For example, it was noted that GLA, DGLA, AA, EPA and DHA when used either in the form of pure fatty acid alone or in the form of fatty acid rich oils could inhibit the growth of skin papilloma in mice, formation and growth of hepatoma in rats and ascitic tumor cells in the peritoneum of experimental animals. These results indicate that these fatty acids can inhibit the growth of a variety of tumors even in vivo. In further studies, it was noted that these fatty acids are able to enhance free radical generation and the lipid peroxidation process selectively in the tumor cells but not so much in the normal cells and thus, are able to bring about their cancer killing action.

This ability of PUFAs to augment free radical generation and lipid peroxidation in the tumor cells is analogous to the anti-tumor action of lymphokines such as tumor necrosis factor (TNF) and interferon (IFN), both alpha and gamma varieties. These lymphokines (also referred to as cytokines) are capable of inducing the release of PUFAs from the cell membrane lipid pool and enhance free radical generation in the cells. Similarly several anti-cancer drugs such as, but not limited to, doxorubicin and vincristine have the capacity to augment free radical generation and promote lipid peroxidation. In addition, PUFAs and their products can modulate immune response, augment a respiratory burst of neutrophils and free radical generation by macrophages. This evidence is further testified by the observation that the incidence of cancer in Eskimos is low as influenced by their traditional diet, which is rich in EPA and DHA. Inventor's studies have shown that PUFAs can be exploited as possible anti-cancer agents either alone or in combination with lymphokines and traditional anti-cancer drugs.

In a series of investigations by the inventor, it was also observed that the cytotoxic action of anti-cancer drugs such as doxorubicin, vincristine and cis-platinum can be augmented by various PUFAs such as GLA, DGLA, AA, EPA and DHA.

In addition, these fatty acids could also enhance the cellular uptake of these anti-cancer drugs by the tumor cells and thus, are able to potentiate the anti-cancer actions of these drugs. In another similar experiment by the inventor, it was also observed that GLA, DGLA, AA, EPA and DHA were able to kill TNF resistant L-929 tumor cells in vitro. Further, these TNF-resistant tumor cells were rendered TNF sensitive by prior treatment of these L-929 cells by GLA, DGLA, AA, EPA and DHA. These results indicate that PUFAs can not only kill the tumor cells by themselves but are also capable of potentiating the cell killing effect of various anti-cancer drugs, lymphokines such as TNF and IFN and also render anti-cancer drug and TNF-resistant tumor cells sensitive to the cytotoxic action of various anti-cancer drugs and lymphokines.

In another set of experiments, it was also noted that vincristine resistant tumor cells, $KB^{chR}$-8-5 (henceforth referred to as KB-8-5 cells) can be made sensitive to the cytotoxic action of vincristine by GLA, DGLA, AA, EPA and DHA. Further, when sub-optimal doses of vincristine and fatty acids were added together to these vincristine resistant cells produced optimal (i.e. significant) cell killing action. This shows that vincristine and other anti-cancer compounds and PUFAs when added together to cancer cells, they potentiate the cytotoxic action of each other. Fatty acid analysis of both vincristine sensitive (KB-3-1) and resistant (KB-8-5) cells revealed that the resistant cells have low amounts of GLA, AA, EPA and DHA compared to the vincristine sensitive tumor cells indicating that a deficiency of these fatty acids may be responsible for their resistance to the cytotoxic actions of anti-cancer drugs. Since, both vincristine sensitive and resistant tumor cells are easily (and to the same extent) killed by various PUFAs in vitro, this demonstrates that even drug-resistant tumor cells can be killed by these fatty acids.

In yet another set of experiments, the inventor also noted that L-929 cells which are resistant to the cytotoxic action of tumor necrosis factor (referred to as TNF-resistant L-929 cells) can also be made sensitive to the cytotoxic action of TNF by pre-treating these cells with various PUFAs. In other words, L-929 cells which are resistant to the cytotoxic action of TNF can be sensitized to the cytotoxic action of TNF by PUFAs. This again indicates that PUFAs can not only kill the tumor cells but can also serve as sensitizing agents rendering various tumor cells responsive to the cytotoxic action of various anti-cancer drugs and lymphokines (cytokines) such as tumor necrosis factor.

It is to be noted in this context that PUFAs can bind to albumin and other proteins and hence, if given intravenously may not be available to be taken up by the tumor cells and consequently may not be able to bring about their cell killing action on the tumor cells. In view of this, it is desirable that PUFAs including GLA should be delivered to the patients in such a manner that it is easily available to the tumor (tumor cells) and is delivered selectively to the tumor cells. It is highly desirable that PUFAs including GLA be given intra-tumorally as was experimentally done in the case of human gliomas, or, intra-arterially by selective intra-arterial infusion as was done experimentally in the case of hepatoma and giant cell tumor of the bone. But, it is also possible that in some cases of cancer such as Hodgkin's and non-Hodgkin's lymphoma wherein the tumor cells are extremely sensitive to the cytotoxic actions of PUFAs, even oral administration may be sufficient as was observed in certain patients. Since, PUFAs can potentiate the cell killing effect of anti-cancer drugs and lymphokines, it is desirable to administer a combination of PUFAs, anti-cancer drugs, lymphokines such as TNF and interferon or other anti-angiogenic agents or a combination thereof with or without a carrier agent such as an oily lymphographic agent as the situation indicates. Further studies have also revealed that PUFAs such as GLA, DGLA and EPA can prevent or ameliorate the side effects of anti-cancer agents such as gamma-radiation and cis-platinum to the bone marrow cells of mice. Thus, it appears that when PUFAs and conventional anti-cancer drugs/agents are given together they not only potentiate the cytotoxic action of each on the tumor cells and thus, produce a synergistic and/or additive action in their ability to eliminate the tumor cells but it will also lead to elimination, reduction or amelioration of the side effects of conventional anti-cancer agents. Since PUFAs are able to potentiate the cytotoxic action(s) of conventional anti-cancer agents and lymphokines, it is also possible that this will lead to a significant reduction in the doses of these latter agents without compromising the ultimate benefit namely, elimination of tumor cells or the tumor.

Some of the phenomena which reduce the efficacy of the cytotoxic action of PUFAs and conventional anti-cancer drugs/agents in vivo as compared to in vitro results include the following:

a. PUFAs when administered orally or intravenously can bind to albumin and other proteins in living beings and may not be available to be taken up by the tumor cells. But this ability of PUFAs to bind to proteins is made use of in the present invention and is detailed below.

b. The cytotoxic action of PUFAs is produced by the augmentation of free radical generation and lipid peroxidation in only tumor cells (but not in normal cells). The intensity of the cytotoxic action is disadvantageously reduced in actual clinical efforts because of inefficient transportation of the fatty acids to the target areas.

c. Continued blood supply to tissue with proliferative cell disorders is not conducive to bringing about a significant amount of necrosis especially if the malignant cells multiply faster than they are being destroyed.

d. It was found from a study reported in a June, 1994 "Cancer letters" publication authored by N. Madhavi and U. N. Das that antioxidants like vitamin E and the superoxide anion quencher, superoxide dismutase (SOD) could completely inhibit free radical generation and lipid peroxidation generated by PUFAs like GLA, EPA and DHA. It appears that selective drug delivery to the target tissue will be conducive to the efficacy of the beneficial action of the PUFAs.

The present invention in one aspect resides in a method of inhibiting blood supply to a tumor by using two types of substances: one a lipid and the other a protein or a peptide both of which have very potent anti-angiogenic action. In addition, the invention also comprises of the steps of: locating an artery which carries major blood supply to the tumor, said artery being one that is proximate to the tumor, and intra-arterially injecting into the located artery a predetermined quantity of a polyunsaturated fatty acid (PUFA) in the form of a solution of at least one PUFA chosen from LA, GLA, DGLA, AA, ALA, EPA, DHA and cis-parinaric acid in combination with a protein/peptide with anti-angiogenic substance(s).

The invention in another aspect resides in a method for treating tumors and for facilitating visualization of remission of the tumor in response to treatment, comprising the steps of:

(a) locating an artery which carries a major portion of blood supply to the tumor and is adjacent to the tumor;

(b) obtaining an initial radiographic image of the tumor region;

(c) injecting into the artery a mixture of (i) an oily lymphographic agent, (ii) a lithium salt solution of at least one PUFA chosen from LA, GLA, DGLA, AA, ALA, EPA, DHA; and cis-parinaric acid (iii) an anti-angiogenic protein/substance which is co-valently linked to the fatty acid or form a mixture (fatty acid+anti-angiogenic protein or peptide).

(d) obtaining second and subsequent radiographic images of the tumor regions after predetermined lapses of time; and comparing the initial radiographic images with the second and subsequent radiographic images to assess the extent of remission of the tumor.

The invention in another aspect resides in a method of causing necrosis in a cancerous tumor by inhibiting blood supply to the tumor, and also by direct cytotoxicity to the tumor cells, comprising the steps of: (a) locating an artery proximate to the tumor which carries major blood supply to the tumor; (b) injecting into the located artery a mixture of (i) an anti-angiogenic protein/peptide; (ii) a lithium salt solution of at least one essential fatty acid chosen from LA, GLA, DGLA, AA, ALA, EPA, DHA and cis-parinaric acid; (c) waiting for a predetermined time period and assessing a degree of necrosis in the tumor by examining by a radiographic study or by other means; and, (d) repeating step (b) if necessary to increase the necrosis.

In yet another aspect, the invention resides in a method of treating a glioma and visualizing remission of the glioma as it responds to treatment, comprising:

(a) obtaining an initial radiographic image of a region containing the glioma;

(b) injecting into the glioma region an admixture of (i) a sodium salt or any other suitable salt solution of at least one polyunsaturated fatty acid chosen from LA, GLA, DGLA, AA, ALA, EPA, DHA and cis-parinaric acid or a combination there of along with an anti-angiogenic protein/peptide;

(c) obtaining second and subsequent radiographic images of the glioma region after predetermined lapses of time; and comparing the initial radiographic pictures which shows the glioma, with second and subsequent radiographic images of the glioma region to visualize and assess the extent of remission of the glioma.

In yet another aspect, the invention resides in a method of treating mammalian cell proliferative disorders using an emulsion of a lithium salt of a PUFA or combinations of PUFAs and a predetermined anti-angiogenic protein/peptide administered parenterally including a subcutaneous route. Preferably, the intra-arterial administration of the admixture containing PUFA(s) is done through a catheter. Also, the artery carrying major blood supply to the tumor is to be understood herein as synonymous to the artery which will supply the tumor feeding vessels. Owing to a phenomenon which is consequent to inhibiting blood supply, the present invention makes it not conducive to the formation of new blood vessels i.e. angiogenesis. The anti-angiogenic protein in different implementations of this invention may be ENDOSTATIN or ANGIOSTATIN or any other anti-angiogenic substance.

DETAILED DESCRIPTION

Essential fatty acids are precursors of eicosanoids and are important structural components of cell membranes. They also provide the substrates for the generation of lipid peroxidation products which have an inhibitory action on cell proliferation. Tumor cells are known to have low delta-6-desaturase activity, an enzyme necessary for the desaturation of dietary linoleic acid (LA, 18:2, n-6) and alpha-linolenic acid (ALA, 18:3, n-3) to their respective products. In an earlier study, the inventor has shown that hepatocarcinogens, diethylnitrosamine (DEN) and 2-acetylaminofluorine (2-AAF), can suppress the activity of delta-6-desaturase and delta-5-desaturase resulting in low levels of gamma-linolenic acid (GLA, 18:3, n-6) and arachidonic acid (AA, 20:4, n-6) and eicosapentaenoic acid (EPA, 20:5, n-3) and docosahexaenoic acid (DHA, 22:6, n-3) in the tumor cells. These results led the inventor and others to study the effect of various fatty acids on the survival of tumor cells in vitro. Addition of EFAs (LA and ALA) and other PUFAs such as GLA, DGLA, AA, EPA, DHA and cis-parinaric acid to a variety of tumor cells in vitro showed that only tumor cells are killed by these fatty acids without harming the normal cells. This selective tumoricidal action of fatty acids seems to be mediated by free radicals and lipid peroxides. Similar to these fatty acids, radiation, some anti-cancer drugs and cytokines (lymphokines) also seem to have the ability to generate free radicals in tumor cells and thus, bring about their tumoricidal actions.

Since drug resistance is a major obstacle in the clinical treatment of cancer and as PUFAs have selective tumoricidal action, the inventor studied the effects of PUFAs on drug-resistant tumor cells and their modulating influence on the actions of anti-cancer drugs. In the above context, in addition to producing reversal of tumor cell drug resistance by the administration of polyunsaturated fatty acids, it is seen from the invention that the manner of targeting the cancerous tissue is very critical to the efficacy and the speed with which necrosis can be brought about. More particularly, it is realized through this invention that by delivering a chosen admixture of salts of predetermined polyunsaturated fatty acids and predetermined anti-angiogenic substance(s) to the tumor site intra-arterially, intra-venously, subcutaneously, intra-peritoneally or by direct injection into the tumor bed, a very beneficial and hitherto unknown effect in terms of inhibiting blood supply to the tumor site and inducing tumor cell lysis is achieved simultaneously.

In clinical studies conducted by the inventor with PUFAs, the inhibition of blood supply was pronounced enough to cause cutting off blood supply to the tumor site with very little time lag. In other instances, an unmistaken strangling of blood supply to the tumor region was observed, but was relatively gradual.

One aspect of the invention consists in the preparation of a combination/composition of treatment of cancer in which one or more of LA, GLA, DGLA, AA, ALA, EPA, DHA and cis-parinaric acid are administered with conventional anti-cancer agents/drugs including anti-angiogenic protein/peptide with or without an oily lymphographic agent or any other suitable agent for the delivery of these compounds; optionally, radiation may be included. The PUFAs may be provided in a daily dose of 0.5 mg to 50 gm together with appropriate doses of conventional anti-cancer drugs such as vincristine, doxorubicin, L-asparaginase, cis-platinum, busulfan, etc., in a daily/weekly/monthly dose of 1 mg to 50 gm depending on the requirement and the stage of the disease and as may be determined from time to time with or without the addition of anti-angiogenic protein/peptide such as ANGIOSTATIN/ENDOSTATIN in a dose of 1 mg to 100 mg/kg of body weight per day. The word anti-angiogenic substance is understood as one or more of the following substances: ANGIOSTATIN, ENDOSTATIN, platelet factor-4, TNP-470, thalidomide, interleukin-12, metalloprotease inhibitors (MMP), anti-adhesion molecules (in their desired dose). The combination of PUFAs, conventional anti-cancer drugs, anti-angiogenic substances and the oily lymphographic agent may be administered by any one or different routes at the same time or at different times and intervals by selecting an appropriate route for each administration or in combination, e.g., oral, parenteral including intra-arterial infusion, intravenous, subcutaneous, intra-peritoneal, topical, anal, vaginal routes as suppositories, or local injection directly into the tumor bed under the guidance of appropriate equipment such as but not limited to radiological guidance (X-rays), CT guidance or MRI guidance or by stereostaxic guidance. The daily dose(s) of these compounds may not exclude the administration of long acting preparations or depot preparation once or more times in a day, week, month or at some other appropriate time interval as determined from time to time depending on the necessity. The fatty acids (PUFAs) may be present in any physiologically acceptable form including but not limited to glycerides, esters, free acids, amides, phospholipids or salts. The conventional anti-cancer drugs may be administered by themselves or in conjugation with PUFAs (either alone or in combination such as GLA alone or GLA+AA, LA, DGLA, ALA, EPA or DHA). Similarly the anti-angiogenic substance (s) may be given by themselves or in conjugation with PUFAs. For intra-arterial infusion or intravenous/subcutaneous injection/infusion or administration of LA, GLA, DGLA, AA, ALA, EPA, DHA and/or cis-parinaric acid these may be given by themselves or in combination or dissolved or conjugated in/with anti-angiogenic substances and in any other suitable solution that can be given parenterally but not limited to them. All these PUFAs, conventional anti-cancer drugs, anti-angiogenic substances and lymphographic agent may each be given alone or in combination thereof or all together or separately at the same time or at different time intervals on the same day/week/month either by same route or different routes as the situation demands.

In order to observe or ascertain and record progress made in patients after administration of admixture according to this invention, images of the affected area e.g., tumor region before and after treatment can be obtained by various known modalities such as computerized axial tomography (CT), magnetic resonance imaging (MRI), etc.

EXAMPLES (1) Hard (wherein the PUFAs have been microencapsulated) or soft gelatin capsules (wherein the fatty acids are present in an oily form) made by accepted normal or forms or methods and are administered to persons suffering from cancer in conjunction with conventional anti-cancer drugs and/or anti-angiogenic substances in the doses as stated supra.

(2) Hard or soft gelatin capsules made by conventional methods, in which the fatty acids, the anti-cancer drugs and anti-angiogenic substances re-incorporated together in the same capsule and are administered to persons suffering from cancer.

(3) As intra-tumoral preparation in appropriate doses (from 0.5 mg to 50 mg per day) of pure LA, GLA, DGLA, AA, ALA, EPA and DHA either individually or in combination thereof especially with anti-angiogenic substances for the treatment of human brain gliomas or any other accessible tumor (e.g., urinary bladder cancer, carcinoma of the esophagus, carcinoma of the lung, breast cancer etc.) by any route by using flexible fiber optic scopes such as bronchoscope, urethroscope, hysteroscope, etc. In the case of tumors of the head and neck the fatty acids are administered either by direct intra-tumoral route or by selective catheterization of the tumor feeding vessel(s) either by femoral, brachial or carotid routes or by subcutaneous route or intravenous route. The PUFAs and anti-angiogenic substances can be given to these patients daily, weekly or monthly or as and when necessary depending on the requirement and response of the patient to the treatment.

(4) Administered as selective intra-arterial infusion or injection into the tumor feeding vessel by femoral, brachial or carotid routes or any other suitable route or in a combination thereof the PUFAs either alone or in combination with anti-cancer drugs/anti-angiogenic substances with or without the oily lymphographic agent or any other suitable agent all in a mixture or in conjugated form(s) (like GLA+any conventional anti-cancer drug or drugs+anti-angiogenic substance, LA/GLA/DGLA/AA/ALA/EPA/DHA/cis-parinaric acid all individually or in combination thereof+conventional anti-cancer drug(s)+anti-angiogenic substance(s)+lymphographic agent, LA/GLA/DGLA/AA/ALA/EPA/DHA/cis-parinaric acid in combination with or conjugated to anti-angiogenic substance(s) or emulsified with or mixed with oily lymphographic agent, LA/GLA/DGLA/AA/ALA/EPA/DHA/cis-parinaric acid alone or in combination thereof in oily lymphographic agent as a mixture or emulsion or as a conjugate(s) and a variety of other combinations thereof. This preparation may be administered daily, weekly or monthly or at some other appropriate time interval.

(5) Topical preparation of PUFAs either alone or in combination thereof with conventional anti-cancer drugs or anti-angiogenic substance(s) in a suitable delivery vehicle in which daily doses (ranging from 0.5 μg to 100 mg) are applied to primary skin cancers including Kaposi's sarcoma locally and/or conventional anti-cancer drugs are given either orally or parenterally.

By the different embodiments of the invention method described supra, it becomes known that:

(i) when PUFAs or cis-EFAs (essential fatty acids described here are also called as cis-fatty acids as by virtue of their structure are referred to as cis-EFAs as they are in cis-configuration) are administered to patients intra-arterially or even otherwise as a combination with anti-angiogenic substance(s), there are less chances of albumin and other proteins binding to the fatty acids. Consequently, PUFAs thus administered using the invention are better available to be taken up by the tumor cells.

(ii) Owing to the efficient transportation of PUFAs to the tumor site as described hereinbefore, there is increased intensity of the cytotoxic action of PUFAs and the administered anti-cancer agents (drugs or anti-angiogenic substance(s) or a combination thereof). Thus, using the invention, there is relatively better augmentation of free radical generation and lipid peroxidation in the tumor cells, thereby facilitating a greater degree of necrosis.

(iii) Inhibiting blood supply to the tumor region by the method of invention prevents cell proliferation in the tumor region, thus enabling healthy tissue to to grow back into place.

(iv) The inhibition otherwise caused by vitamin E and superoxide dismutase to free radical generation and lipid peroxidation produced by PUFAs, is reduced in the method of this invention because of the manner of transportation of PUFAs to the tumor site in combination with anti-angiogenic substance(s) intra-arterially through a proximate artery or intravenously or subcutaneously.

It is also within the purview of this invention, as stated supra to administer an admixture of PUFAs, anti-cancer drugs, and selected anti-angiogenic substance(s) at the same time, administering predetermined doses of PUFAs orally. All such variations are envisaged to be within the ambit of this invention.

Application to mammals: Even though the examples described supra relate to humans, it is envisaged that the method of inhibiting blood supply and using admixture of this invention including an anti-angiogenic substance are equally applicable to other mammals.

EQUIVALENTS

While this invention has been particularly shown and described with reference to preferred embodiments thereof, it will be understood by those skilled in the art that various changes in form and details may be made therein without departing from the spirit and scope of the invention as defined by the appended claims. Also sodium and potassium salts are considered equivalents of each other. Imaging techniques referred to herein are intended to include CAT, MRI, X-rays and other possible imaging methods. Those skilled in the art will recognize or be able to ascertain using no more than routine experimentation, many equivalents to the specific embodiments of the invention described specifically herein. Such equivalents are intended to be encompassed in the scope of the appended claims.

REFERENCES

1. Battegay E J. Angiogenesis: mechanistic insights, neovascular diseases, and therapeutic prospects. J Mol Med 1995; 73: 333-346.
2. O'Reilly M S, Boehm T, Shing Y, Fukai N, Vasios G, Lane W S, Flynn E, Birkhead J R, Olsen B R, Folkman J. Endostatin: an endogenous inhibitor of angiogenesis and tumor growth. Cell 1997; 88: 277-285.
3. Sim B K, O'Reilly M S, Liang H, Fortier A H, He W, Madsen J W, Lapcevich R, Nacy C A. A recombinant human Angiostatin protein inhibits experimental primary and metastatic cancer. Cancer Res 1997; 57: 1329-1334.
4. Bicknell R, Harris A L. Mechanisms and therapeutic implications of angiogenesis. Curr Opin Oncol 1996; 8: 60-65.
5. Gately S, Twardowski P, Stack M S, Patrick M, Boggio L, Cundiff D L, Schnaper H W, Madison L, Volpert O, Bouck N, Enghild J, Kwaan H C, Soff G A. Human prostate carcinoma cells express enzymatic activity that converts human plasminogen to the angiogenesis inhibitor, angiostatin. Cancer Res 1996; 56: 4887-4890.
6. O'Reilly M S, Holmgren L, Chen C, Folkman J. Angiostatin induces and sustains dormancy of human primary tumors in mice. Nature Med 1996; 2: 689-692.
7. O'Reilly M S. Angiostatin: an endogenous inhibitor of angiogenesis and of tumor growth. EXS 1997; 79: 273-294.
8. Wu Z, O'Reilly M S, Folkman J, Shing Y. Suppression of tumor growth with recombinant murine angiostatin. Biochem Biophys Res Commun 1997; 236: 651-654.
9. Gately S, Twardowski P, Stack M S, Cundiff D L, Grella D, Castellino F J, Enghild J, Kwaan H C, Lee F, Kramer R A, Volpert O, Bouck N, Soff G A. The mechanism of cancer-mediated conversion of plasminogen to the angiogenesis inhibitor angiostatin. Proc Natl Acad Sci USA 1997; 94: 10868-10872.
10. Lannutti B J, Gately S T, Quevedo M E, Soff G A, Paller A S. Human ANGIOSTATIN inhibits murine hemangioendothelioma tumor growth in vivo. Cancer Res 1997; 57: 5277-5280.

11. Luo J, Lin J, Paranya G, Bischoff J. angiostatin upregulates E-selectin in proliferating endothelial cells. Biochem Biophys Res Commun 1998; 245: 906-911.
12. Rivas M J, Arii S, Furutani M, Harada T, Mizumoto M, Nishiyama H, Fujita J, Imamura M. Expression of human macrophage metalloelastase gene in hepatocellular carcinoma: correlation with angiostatin generation and its clinical significance. Hepatology 1998; 28: 986-993.
13. Sang Q X. Complex role of matrix metalloproteinases in angiogenesis. Cell Res 1998; 8: 171-177.
14. Cornelius L A, Nehring L C, Harding E, Bolanowski M, Welgus H G, Kobayashi D K, Pierce R A, Shapiro S D. Matrix metalloproteinases generate ANGIOSTATIN: effects on neovascularization. J Immunol 1998; 161: 6845-6852.
15. Lucas R, Holmgren L, Garcia I, Jimenez B, Mandriota S J, Borlat F, Sim B K, Wu Z, Grau G E, Shing Y, Soff G A, Bouck N, Pepper M S. Multiple forms of angiostatin induce apoptosis in endothelial cells. Blood 1998; 92: 4730-4741.
16. Moser T L, Stack M S, Asplin I, Enghild J J, Hojrup P, Everitt L, Hubchak S, Schnaper H W, Pizzo S V. Angiostatin binds ATP synthase on the surface of human endothelial cells. Proc Natl Acad Sci USA 1999; 96: 2811-2816.
17. Stack M S, Gately S, Bafetti L M, Enghild J J, Soff G A. Angiostatin inhibits endothelial and melanoma cellular invasion by blocking matrix-enhanced plasminogen activation.

Biochem J 1999; 340: 77-84.
18. O'Mahony C A, Albo D, Tuszynski G P, Berger D H. Transforming growth factor-beta 1 inhibits generation of angiostatin by human pancreatic cancer cells. Surgery 1998; 124: 388-393.
19. Twining S S, Wilson P M, Ngamkitidechakul C. Extrahepatic synthesis of plasminogen in the human cornea is up-regulated by interleukins-1alpha and-1beta. Biochem J 1999; 339: 705-712.
20. Cao Y. Therapeutic potentials of angiostatin in the treatment of cancer. Haematologica 1999; 84: 643-650.
21. Andre T, Chastre E, Kotelevets L, Vaillant J C, Louvet C, Balosso J, LeGall E, Prevot S, Gespach C. Tumoral angiogenesis: physiopathology, prognostic value and therapeutic perspectives. Rev Med Interne 1998; 19: 904-913.
22. Mauceri H J, Hanna N N, Beckett M A, Gorski D H, Staba M J, Stellato K A, Bigelow K, Heimann R, Gately S, Dhanabal M, Soff G A, Sukhatme V P, Kufe D W, Weichselbaum R R. Combined effects of angiostatin and ionizing radiation in antitumour therapy. Nature 1998; 394: 287-291.
23. Gorski D H, Mauceri H J, Salloum R M, Gately S, Hellman S, Beckett M A, Sukhatme V P, Soff G A, Kufe D W, Weichselbaum R R. Potentiation of the antitumor effect of ionizing radiation by brief concomitant exposures to angiostatin. Cancer Res 1998; 58: 5686-5689.
24. Nguyen J T, Wu P, Clouse M E, Hlatky L, Terwilliger E F. Adeno-associated virus-mediated delivery of antiangiogenic factors as an antitumor strategy. Cancer Res 1998; 58: 5673-5677.
25. Chen Q R, Kumar D, Stass S A, Mixson A J. Liposomes complexed to plasmids encoding angiosatin and endostatin inhibit breast cancer in nude mice.

Cancer Res 1999; 59: 3308-3312.
26. Gasparini G. The rationale and future potential of angiogenesis inhibitors in neoplasia. Drugs 1999; 58: 17-38.
27. Begin M E, Das U N, Ells G, Horrobin D F. Selective killing of tumor cells by polyunsaturated fatty acids. Prostaglandins Leukot Med 1985; 19: 177-186.
28. Begin M E, Das U N, Ells G. Cytotoxic effects of essential fatty acids (EFA) in mixed cultures of normal and malignant human cells.

Prog Lipid Res 1986; 25: 573-577.
29. Begin M E, Ells G, Das U N, Horrobin D F. Differential killing of human carcinoma cells supplemented with n-3 and n-6 polyunsaturated fatty acids. J Natl Cancer Inst 1986; 77: 105-
30. Das U N. Tumoricidal action of cis-unsaturated fatty acids and its relationship to free radicals and lipid peroxidation. Cancer Lett 1991; 56: 235-243.
31. Das U N. Gamma-linolenic acid, arachidonic acid and eicosapentaenoic acid as potential anti-cancer drugs. Nutrition 1990; 6: 429-434.
32. Sangeetha P S and Das U N. Cytotoxic action of cis-unsaturated fatty acids on human cervical (HeLa) carcinoma cells in vitro. Prostaglandins Leukot Essen Fatty Acids 1995; 53: 287-299.

Patents
1. O'Reilly; Michael S, Folkman; M. Judah. Angiostatic protein. U.S. Pat. No. 5,639,725, date: Jun. 17, 1997.
2. O'Reilly; Michael S, Folkman; M. Judah. Therapeutic anti-angiogenic compositions and methods. U.S. Pat. No. 5,854,205, date: Dec. 29, 1998.

The invention claimed is:

1. A method of inhibiting blood supply to a tumor, comprising:
   (a) Locating an artery which carries major blood supply to the tumor, said artery being one that is proximate to the tumor;
   and
   (b) Intra-arterially injecting into located artery a predetermined quantity of one or more anti-angiogenic substance(s), and a predetermined quantity of a salt of at least one polyunsaturated fatty acid chosen from linoleic acid, gamma-linolenic acid, dihomo-gamma-linolenic acid, arachidonic acid, alpha-linolenic acid, eicosapentaenoic acid, docosahexaenoic acid, and cis-parinaric acid.

2. A method as in claim 1 wherein said polyunsaturated fatty acid is in the form of a lithium salt solution and wherein said fatty acid is in a range of 0.5 mg to 50 gm.

3. A method as in claim 1 wherein said (b) comprises intra-arterially injecting said predetermined quantity of the polyunsaturated fatty acid and in the form of a lithium salt solution of a polyunsaturated fatty acid, wherein said anti-angiogenic substances is provided in an amount of 1 to 1000 mg/kg/body weight, said solution of polyunsaturated fatty acid further comprising a substance chosen from glycerides, esters, free acids, amides, phospholipids, and salts.

4. A method as in claim 1, wherein the polyunsaturated fatty acid is in the form of a lithium salt solution containing said anti-angiogenic substance(s) and an anti-cancer drug predetermined quantity of said anti-angiogenic substance chosen from: an anti-angiogenic substance naturally occurring as a protein, platelet factor-4, TNP-470, thalidomide, interleukin-12, and metalloprotease inhibitors, and a predetermined anti-cancer drug.

5. A method of treating a tumor and facilitating visualization of remission of the tumor response to treatment, comprising:
   (a) Locating an artery which carries a major portion of blood supply to said tumor and is adjacent to the tumor;

(b) Obtaining an initial radiographic image of tumor;
(c) Injecting into located artery a mixture of at least
   (i) an oily lymphographic agent as a carrier containing one or more of anti-angiogenic substance(s) and
   (ii) a lithium salt solution of at least one polyunsaturated fatty acid chosen from linoleic acid, gamma-linolenic acid, dihomo-gamma-linolenic acid, arachidonic acid, alpha-linolenic acid, eicosapentaenoic acid, docosahexaenoic acid, and cis-parinaric acid
(d) obtaining second and subsequent radiographic images of the tumor after predetermined lapses of time; and
(e) comparing the initial radiographic image with the second and the subsequent images to assess an extent of said remission of the tumor.

6. A method as in clam 5 wherein step (c) comprises intra-arterially injecting said mixture containing, causing anti-angiogenic action by inhibiting the blood supply to the tumor, wherein further the oily lymphographic agent acts as a carrier for said lithium salt solution of predetermined quantities of said polyunsaturated fatty acids.

7. A method of treating a cancerous tumor, comprising
(a) using an oily lymphographic agent as a carrier for
   (i) at least one polyunsaturated fatty acid chosen from a lithium salt of at least one of linoleic acid, gamma-linolenic acid, dihomo-gamma-linolenic acid, arachidonic acid, alpha-linolenic acid, eicosapentaenoic acid, docosahexaenoic acid, and cis-parinaric acid; and
   (ii) a predetermined anti-cancer drug, and anti-angiogenic substances mixed with the polyunsaturated fatty acids or coupled with fatty acids; and
(c) administering by injecting into said cancerous tumor a predetermined quantity of the fatty acids, the anti-cancer drug and predetermined said anti-angiogenic substance in the oily lymphographic agent as a carrier.

* * * * *